United States Patent
Schmid et al.

(10) Patent No.: US 11,559,435 B2
(45) Date of Patent: Jan. 24, 2023

(54) SYSTEMS AND METHODS FOR FEMTOSECOND LASER OPHTHALMIC SURGERY DOCKING

(71) Applicant: Alcon Inc., Fribourg (CH)

(72) Inventors: Stefan Schmid, Neuendettelsau (DE); Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 153 days.

(21) Appl. No.: 16/333,968

(22) PCT Filed: Oct. 19, 2016

(86) PCT No.: PCT/IB2016/056300
§ 371 (c)(1),
(2) Date: Mar. 15, 2019

(87) PCT Pub. No.: WO2018/073625
PCT Pub. Date: Apr. 26, 2018

(65) Prior Publication Data
US 2019/0247233 A1 Aug. 15, 2019

(51) Int. Cl.
*A61F 9/008* (2006.01)
*A61F 9/009* (2006.01)

(52) U.S. Cl.
CPC .......... *A61F 9/00836* (2013.01); *A61F 9/009* (2013.01); *A61F 9/00825* (2013.01); *A61F 2009/00846* (2013.01)

(58) Field of Classification Search
CPC .. A61F 9/00836; A61F 9/00825; A61F 9/009; A61F 2009/00846
See application file for complete search history.

(56) References Cited

U.S. PATENT DOCUMENTS

| | | |
|---|---|---|
| 6,283,954 B1 | 9/2001 | Yee |
| 2005/0024586 A1 | 2/2005 | Teiwes |
| 2010/0274228 A1* | 10/2010 | Mrochen ................ A61F 9/013 604/541 |

(Continued)

FOREIGN PATENT DOCUMENTS

| | | |
|---|---|---|
| CN | 102843955 A | 12/2012 |
| CN | 103167851 A | 6/2013 |

(Continued)

*Primary Examiner* — Lynsey C Eiseman
*Assistant Examiner* — Jessandra F Hough

(57) ABSTRACT

The present disclosure provides a system for femtosecond ophthalmic surgery in which a measuring device and a camera generate data that is processed and used to create an enhanced pictorial representation based on the actual positions of the suction ring and the eye. The pictorial representation may include a graphic relating to ophthalmic surgery, such as for a flap or an incision. The disclosure further provides a method for docking a suction ring in femtosecond laser ophthalmic surgery, which includes observing and generating data relating to the position of the suction ring, generating data relating to a pictorial representation of the suction ring and the eye, processing the data relating to the observed position and the pictorial representation to generate an enhanced pictorial representation, and presenting it during surgery. The pictorial representation may include a graphic relating to ophthalmic surgery, such as for a flap or an incision.

15 Claims, 5 Drawing Sheets

(56) References Cited

U.S. PATENT DOCUMENTS

| | | |
|---|---|---|
| 2011/0187995 A1 | 8/2011 | Frey |
| 2011/0304819 A1 | 12/2011 | Juhasz |
| 2012/0167327 A1 | 7/2012 | Kasack et al. |
| 2013/0050649 A1 | 2/2013 | Juhasz |
| 2013/0338649 A1* | 12/2013 | Hanebuchi ............ A61F 9/0084 606/4 |
| 2014/0128731 A1* | 5/2014 | Gonzalez ............... A61B 3/107 600/427 |
| 2014/0128852 A1* | 5/2014 | Gooding ................ A61F 9/008 606/4 |
| 2014/0276677 A1 | 9/2014 | Brownwell et al. |
| 2016/0095752 A1 | 4/2016 | Srinivasan |
| 2018/0085257 A1* | 3/2018 | Horvath ............. A61F 9/00834 |

FOREIGN PATENT DOCUMENTS

| | | |
|---|---|---|
| CN | 103957774 A | 7/2014 |
| EP | 1970034 A1 | 9/2008 |
| EP | 2477587 A1 | 7/2012 |
| JP | 2013248303 A | 12/2013 |
| JP | 2014525286 A | 9/2014 |
| WO | 20160061552 A1 | 4/2016 |
| WO | 2016159331 A1 | 10/2016 |

* cited by examiner 103  405  410  415

103  405  410  415

SYSTEMS AND METHODS FOR FEMTOSECOND LASER OPHTHALMIC SURGERY DOCKING

TECHNICAL FIELD

The present disclosure relates to ophthalmic surgery and surgical equipment, and more specifically, to systems and methods for docking a suction cone on an eye during femtosecond laser ophthalmic surgery.

BACKGROUND

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's vision after the surgery.

One type of ophthalmic surgery, refractive eye surgery, is used to correct a variety of vision problems. One common such refractive surgery is known as LASIK (laser-assisted in situ keratomileusis) and is used to correct myopia and hyperopia, astigmatism, or more complex refractive errors. Other ophthalmic surgeries may correct corneal defects or other problems. For instance, phototherapeutic keratectomy (PTK) may be used to remove diseased corneal tissue or corneal irregularities either alone or in combination with LASIK. Another common ophthalmic surgery is the removal of cataracts.

During LASIK, PTK, cataract surgery, and other ophthalmic surgeries, corrective procedures are commonly performed on interior parts of the eye, such as the corneal stroma or the lens, rather than on the eye surface. This practice tends to improve surgical outcomes by allowing the corrective procedure to be targeted to the most effective part of the eye, by keeping the outer, protective parts of the cornea largely intact, and for other reasons.

The interior part of the eye may be accessed in a variety of manners, but frequently access involves cutting a flap in the cornea or otherwise cutting the cornea. Corneal cutting is often performed by a femtosecond laser that creates focused ultrashort pulses, eliminating collateral damage of surrounding tissues associated with slower lasers and complications associated with mechanical cutting instruments, such as blades. Femtosecond lasers can therefore be used to dissect tissue on a microscopic level.

Femtosecond laser ophthalmic surgery typically includes docking, imaging, analysis, and laser treatment.

During docking, a patient's eye is docked to a suction cone in order to provide pressure to flatten the patient's cornea (known as applanation) and hold it in position for the laser treatment. A curved suction cone, which does not flatten the cornea, may also be used for the docking process. Docking is a sensitive process, and proper placement of the suction cone is important for successful femtosecond laser ophthalmic surgery. However, correct placement of the suction cone is currently typically guided through visual inspection by the user, relying on experience and perception.

SUMMARY

The present disclosure provides a system for femtosecond laser ophthalmic surgery. The system includes a suction ring, a measuring device operable to observe an observed position of the suction ring and generate data relating to the observed position, a camera operable to generate data relating to a pictorial representation of the suction ring and an eye within the detection frame of the camera, a processor operable to process data relating to the observed position and the pictorial representation to create an enhanced pictorial representation based on the positions of the suction ring and the eye, and a display operable to receive the enhanced pictorial representation when transmitted from the processor and to present the enhanced pictorial representation during femtosecond laser ophthalmic surgery.

In additional embodiments, which may be combined with one another unless clearly exclusive: the measuring device includes a gyroscopic system, an ultrasonic system, at least one force transducer, or a combination thereof; the camera includes multiple cameras, cameras with autofocus, an eye tracking system, or combinations thereof; the display includes a screen, a heads-up display, or a combination thereof; the processor is operable to create and the display is operable to present an enhanced pictorial representation in real time; the processor is further operable to process data relating to the observed position of the suction ring in the x-y plane, defined as a plane roughly perpendicular to the apex of the cornea, to create an enhanced pictorial representation based on the position of the suction ring and the display is operable to display the enhanced pictorial representation; the processor is further operable to include a graphic relating to ophthalmic surgery with the enhanced pictorial representation transmitted and the display is further operable to present an enhanced pictorial representation including a graphic relating to ophthalmic surgery; and the graphic may be for a flap or for an incision.

The present disclosure further provides a method for docking a suction ring in femtosecond laser ophthalmic surgery. The method includes observing an observed position of a suction ring in an x-y plane defined with respect to an eye, using a measuring device, generating data relating to the observed position of the suction ring using the measuring device, generating data relating to a pictorial representation of the suction ring and an eye within a detection frame of a camera, processing the data relating to the observed position of the suction ring and data relating to the pictorial representation to create an enhanced pictorial representation based on an actual position of the suction ring and the eye, and transmitting the pictorial representation from the processor to a display that presents the pictorial representation.

In additional embodiments, which may be combined with one another unless clearly exclusive: observing an observed position of a suction ring includes observing tilt affecting the observed position, in relation to the x-y plane; creating and transmitting the enhanced pictorial representation is in real time; transmitting the enhanced pictorial representation from the processor to the display includes transmitting the enhanced pictorial representation with a graphic relating to ophthalmic surgery; and the graphic relating to ophthalmic surgery is for a flap or an incision.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

Figure 1:
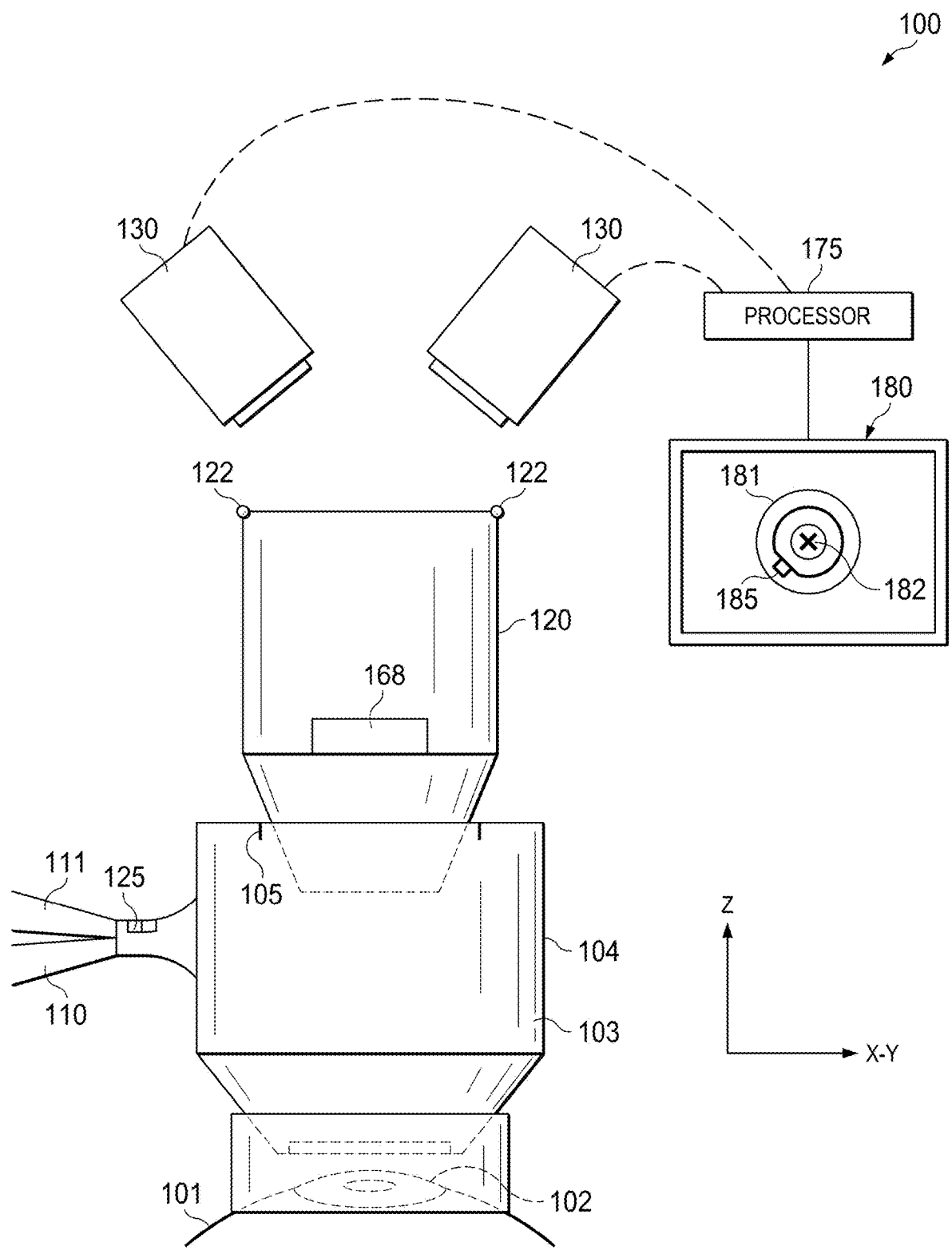
FIG. 1 is a schematic representation of elements of a system for femtosecond laser ophthalmic surgery.

The present disclosure provides systems and methods for docking a suction cone on an eye during femtosecond laser ophthalmic surgery. In docking the suction cone on the eye, a suction ring is first docked on the eye in a correct position in the x-y plane, which is defined as a plane roughly perpendicular to the apex of the cornea, as illustrated in FIG. 1. The system provides a measuring device that observes an observed position of a suction ring and generates data relating to the observed position, and a camera that generates data relating to a pictorial representation of the suction ring and an eye within a detection frame of the camera. The system further provides a display and a processor that processes the data relating to the observed position of the suction ring and the data relating to the pictorial representation, to create an enhanced pictorial representation based on the actual position of the suction ring and the eye. This enhanced pictorial representation is transmitted to the display. The enhanced pictorial representation may include graphics relating to ophthalmic surgery, for example, a graphic for a flap or an incision.

FIG. 1 is a schematic diagram of a system 100 for docking a suction cone 120 on an eye for femtosecond laser ophthalmic surgery. As shown, system 100 includes a suction ring 103 which is suctioned to an eye 101, where a lens 102 and patient interface 104 fit within the suction ring 103. System 100 further provides a measuring device to observe an observed position of the suction ring in the x-y plane, defined as a plane roughly perpendicular to the apex of the cornea. The measuring device may be a gyroscopic system 125, an ultrasonic system 168, at least one force transducer 122, or any combination thereof. The measuring device may transmit data relating to the observed position to processor 175. Cameras 130 may generate data relating to a pictorial representation of the suction ring and the eye within the detection frame of the camera and transmit data relating to the pictorial representation to processor 175. Processor 175 processes the data received, relating to the observed position and the pictorial representation, to create an enhanced pictorial representation based on the actual positions of the suction ring and the eye. Processor 175 transmits the enhanced pictorial representation to display 180 for presentation. The enhanced pictorial representation may include a graphic relating to ophthalmic surgery. For instance, a graphic for cutting a flap 185. The graphic relating to ophthalmic surgery may be superimposed or presented on any part of the enhanced pictorial representation.

Suction ring 103 may be positioned on the eye manually or via a control device. If positioned manually, the suction ring may be handled directly or with a handling device, such as forceps. If positioned via a control device, the suction ring may be connected to an electronically controlled assembly. The electronically controlled assembly may be used to adjust the position of the suction ring instead of manually handling the suction ring.

Measuring device 120 may be a cable-connected or wireless system. If wireless, measuring device 120 may include a receiver and a sensor capable of transmitting data sensed to the receiver. The measuring device may be a gyroscopic system 125, an ultrasonic system 168, at least one force transducer 122, or any combination thereof. As shown in FIG. 1, wireless gyroscopic system 125 may observe an observed position of the suction ring in the x-y plane and transmit data relating to the observed position to processor 175. Ultrasonic system 168 may detect and measures distance of at least three positions of the suction ring by evaluating the amount of time it takes for sound to travel. Ultrasonic system 168 transmits data relating to the observed position to processor 175. Once suction cone 120 contacts patient interface 104, attached to the suction ring, force transducers 122 may detect points of contact and transmit data relating to detected points of contact to processor 175.

Camera 130 generates data relating to a pictorial representation of the suction ring and an eye within a detection frame of the camera, and transmits the data to processor 175. Camera 130 may be one or more cameras. Camera 130 may be an eye tracking system. Camera 130 may have autofocus, which would allow it to detect the interval distance between the suction ring and the eye and adjust focus as a function of the interval distance. Two cameras are shown in FIG. 1. Cameras 130 may be arranged in such a manner that the position of the suction ring may be stereoscopically detected by processor 175. Processor 175 may also detect the position of the suction ring by object recognition. The suction ring may include markings 105 to assist in detection and evaluation.

Processor 175 receives and processes data from the measuring device and cameras 130. Processor 175 processes data of the observed position of the suction ring in the x-y plane and data relating to the pictorial representation of the suction ring and the eye within a detection frame of the camera, to create an enhanced pictorial representation based on the actual positions of the suction ring and the eye.

The pictorial representation may further include a graphic relating to ophthalmic surgery. For instance, a graphic for cutting a flap 185, or a graphic for making an incision, as shown in FIG. 3. A graphic for cutting a flap may be used in instances where the surgical procedure requires access to a large area of the cornea. A graphic for making an incision may be used in instances where the surgical procedure requires access to interior structures of the eye, such as the cornea. The graphic may be superimposed or presented on any part of the pictorial representation. Processor 175 transmits the pictorial representation to display 180 to present during ophthalmic surgery.

Processor 175 may comprise, for example a microprocessor, microcontroller, digital signal processor (DSP), application specific integrated circuit (ASIC), or any other digital or analog circuitry configured to interpret and/or execute program instructions and/or process data. In some embodiments, processor 175 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

As illustrated in FIG. 1, display 180 presents the pictorial representation of the position of the suction ring in the x-y plane 181, including a graphic for cutting flap 185. Graphic for cutting a flap 185 indicates that the suction ring is centered, in relation to a user-selected centering axis. For example, the suction ring may be centered in relation to the center of the eye 182 or in relation to the visual axis of the patient. Because the visual axis of a patient often does not pass through the absolute center of the patient's eye, the suction ring may be centered in relation to the visual axis of the patient, as an alternative to the center of the eye. One or more of these pictorial representations may be presented on a display 180 in real time during the femtosecond laser ophthalmic surgery. Display 180 may include multiple displays and may be a screen, a heads-up display, or a combination.

Figure 2A:
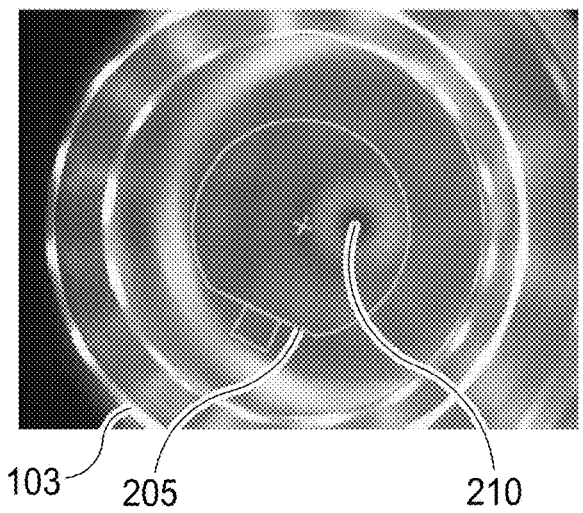
FIG. 2A is a digitally processed image of the eye during docking, the image including a graphic for cutting a flap.

FIG. 2A is a digitally processed image of the eye during docking, the image including a graphic 205 for cutting a flap. The graphic indicates that suction ring 103, as suctioned to the eye, is not centered in the x-y plane. Although suction ring 103 may be centered in relation to a user-selected centering axis (here, the center of the eye 210), as shown, the suction ring may still not be centered in relation to the optics center of the femtosecond laser.

Figure 2B:
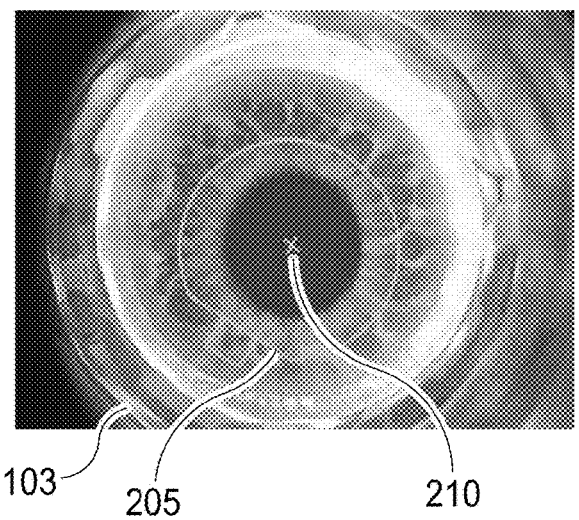
FIG. 2B is a digitally processed image of the eye when the suction cone is docked, the image including a graphic for cutting a flap.

FIG. 2B is a digitally processed image of the eye when the suction cone is docked to the eye, the image including a graphic 205 for an incision. The graphic indicates that suction ring 103 is centered in relation to the user-selected centering axis (here, the center of the eye 210), and the optic center of the femtosecond laser.

Figure 3A:
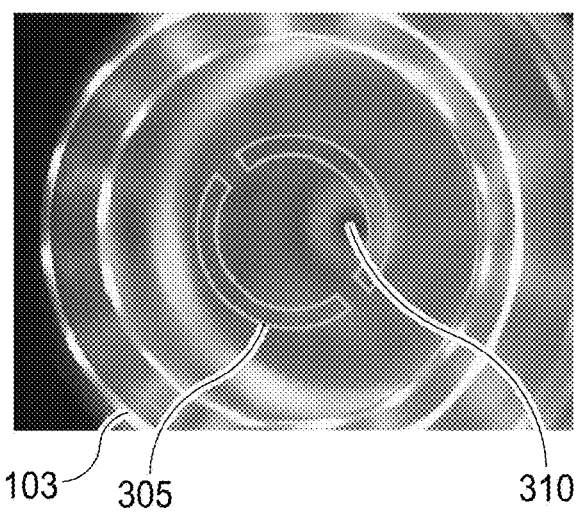
FIG. 3A is a digitally processed image of the eye during docking, the image including a graphic for an incision.

FIG. 3A is a digitally processed image of the eye during docking, the image including a graphic 305 for an incision. The graphic indicates that suction ring 103, as suctioned to the eye, is not centered in the x-y plane. Although suction ring 103 may be centered in relation to a user-selected centering axis (here, the center of the eye 310), as shown, the suction ring may still not be centered in relation to the optics center of the femtosecond laser.

Figure 3B:
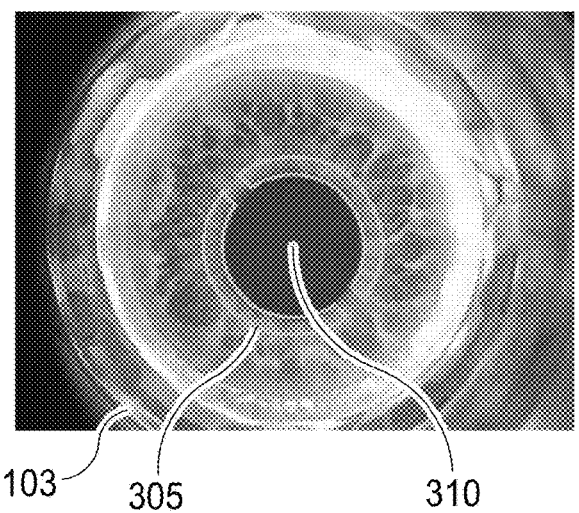
FIG. 3B is a digitally processed image of the eye when the suction cone is docked, the image including a graphic for an incision.

FIG. 3B is a digitally processed image of the eye when the suction cone is docked to the eye, the image including a graphic 305 for an incision. The graphic indicates that suction ring 103 is centered in relation to the user-selected centering axis (here, the center of the eye 310), and the optic center of the femtosecond laser.

Figure 4A:
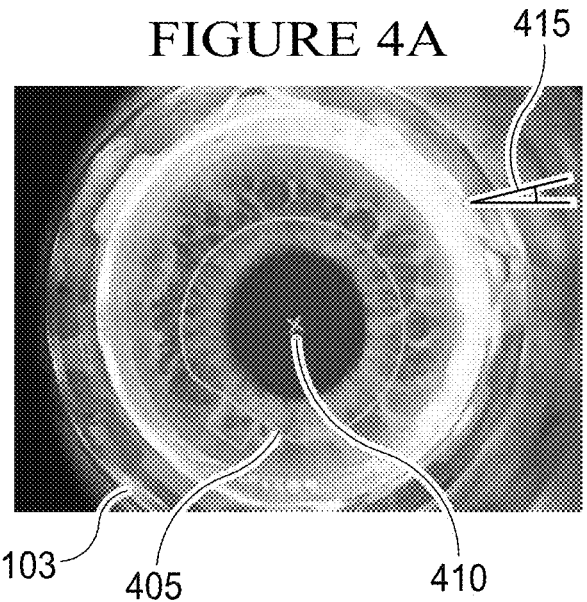
FIG. 4A is a digitally processed image of the eye when the suction cone is docked, the image including a graphic indicating tilt.

FIG. 4A is a digitally processed image of the eye when the suction cone is docked to the eye, the image including a graphic 405 for cutting a flap. The image indicates that suction ring 103 is centered in relation to the user-selected centering axis (here, the center of the eye 410) and the optics center of the femtosecond laser. However, angle 415 indicates that the suction ring is tilted in relation to the x-y plane. Angle 415 may indicate that the suction ring is tilted upward or downward in relation to the x-y plane.

Figure 4B:
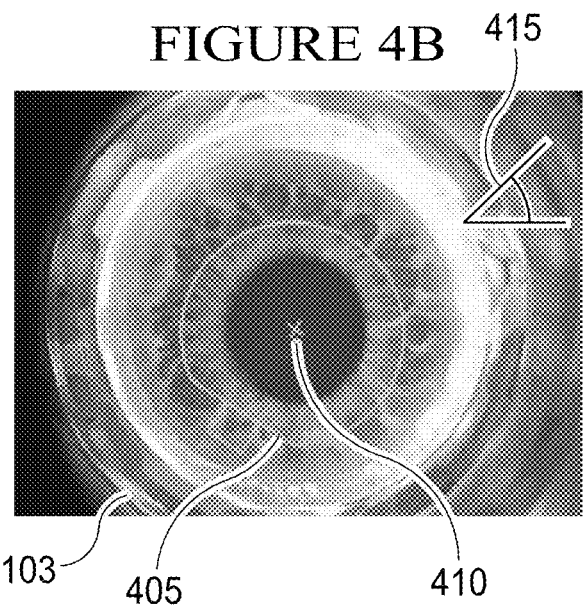
FIG. 4B is a digitally processed image of the eye when the suction cone is docked, the image including a graphic indicating a greater degree of tilt than shown in FIG. 4A.

FIG. 4B is a digitally processed image of the eye when the suction cone is docked to the eye, the image including a graphic 405 for cutting a flap. The image indicates that suction ring 103 is centered in relation to the user-selected centering axis (here, the center of the eye 410) and the optics center of the femtosecond laser. However, angle 415 indicates that the suction ring is tilted in relation to the x-y plane, the degree of tilt being greater than that shown in FIG. 4A. Angle 415 may indicate that the suction ring is tilted upward or downward in relation to the x-y plane.

Figure 5A:
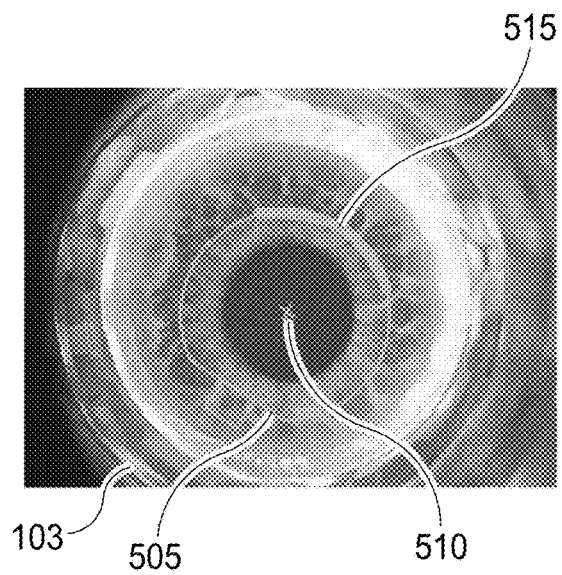
FIG. 5A is a digitally processed image of the eye when the suction cone is docked, the image including a graphic indicating tilt in the lines of the graphic.

FIG. 5A is a digitally processed image of the eye when the suction cone is docked to the eye, the image including a graphic 505 for cutting a flap. The image indicates that suction ring 103 is centered in relation to the user-selected centering axis (here, the center of the eye 510) and the optics center of the femtosecond laser. However, graphic line 515, thicker than the rest of the graphic, indicates that the suction ring is tilted in relation to the x-y plane, in the direction of line 515. Graphic line 515 may indicate that the suction ring is tilted upward or downward in relation to the x-y plane.

Figure 5B:
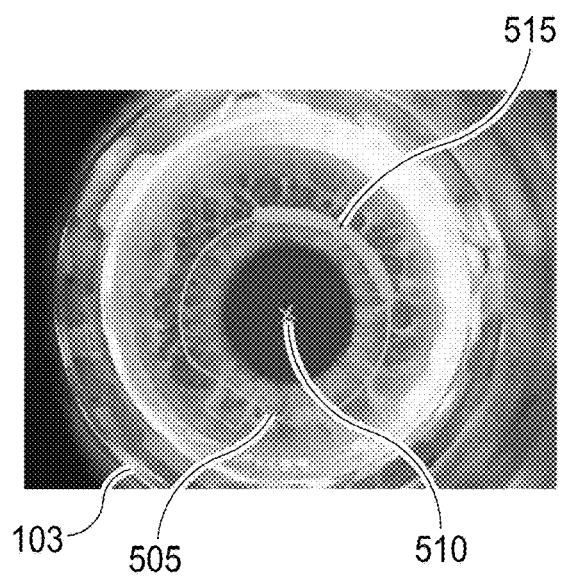
FIG. 5B is a digitally processed image of the eye when the suction cone is docked, the image including a graphic indicating a greater degree of tilt in the lines of the graphic than shown in FIG. 5A.

FIG. 5B is a digitally processed image of the eye when the suction cone is docked to the eye, the image including a graphic 505 for cutting a flap. The image indicates that suction ring 103 is centered in relation to the user-selected centering axis (here, the center of the eye 510) and the optics center of the femtosecond laser. However, graphic line 515, thicker than the rest of the graphic, indicates that the suction ring is tilted in relation to the x-y plane, in the direction of line 515. In FIG. 5B, graphic line 515 is thicker than graphic line 515 in FIG. 5A, which indicates that the degree of tilt in relation to the x-y plane is greater in FIG. 5B than in FIG. 5A. Graphic line 515 may indicate that the suction ring is tilted upward or downward in relation to the x-y plane.

Figure 5C:
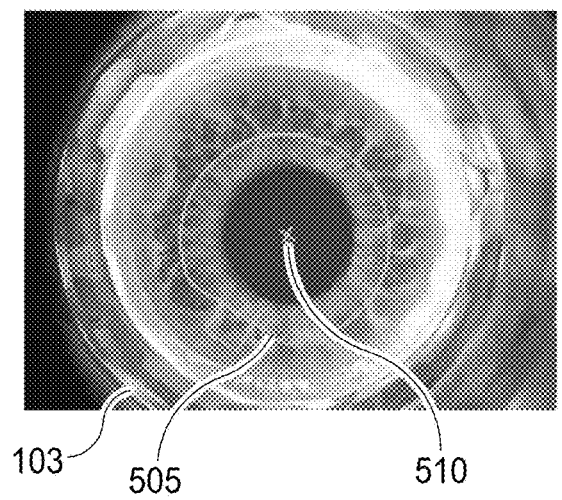
FIG. 5C is a digitally processed image of the eye when the suction cone is docked, the image including a graphic indicating no tilt.

FIG. 5C is a digitally processed image of the eye when the suction cone is docked to the eye, the image including a graphic 505 for cutting a flap. The image indicates that suction ring 103 is centered in relation to the user-selected centering axis (here, the center of the eye 510) and the optics center of the femtosecond laser. All graphic lines are of equal thickness indicating that the suction ring is not tilted in relation to the x-y plane.

Figure 6:
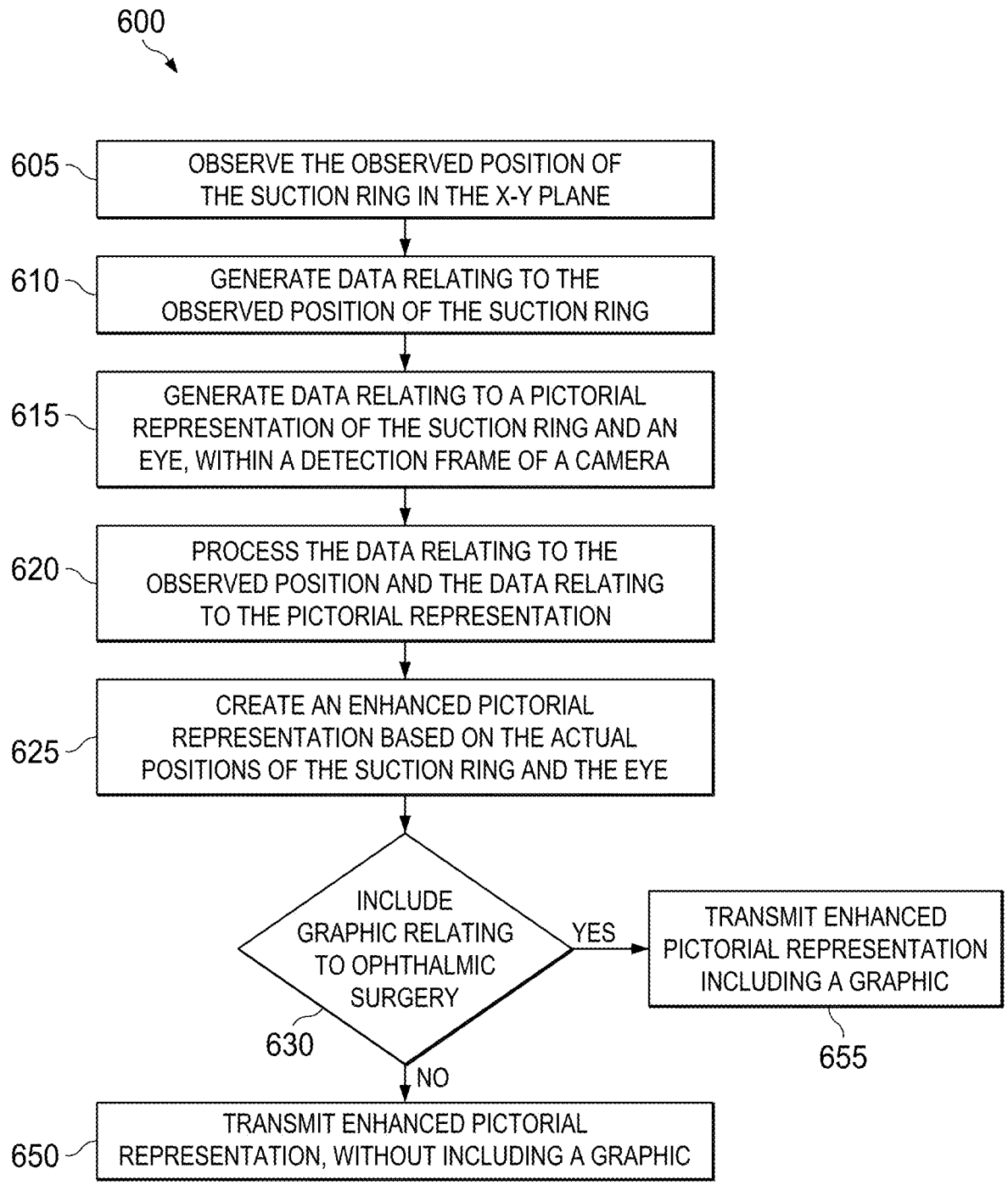
FIG. 6 is a flow chart of a method for docking on an eye in femtosecond laser ophthalmic surgery.

FIG. 6 is a flow chart of a method for docking a suction ring on an eye in femtosecond laser ophthalmic surgery. At step 605, an observed position, of the suction ring in the x-y plane defined with respect to the eye, is observed. At step 610, data relating to the observed position of the suction ring is generated. At step 615, data relating to a pictorial representation of the suction ring and an eye within a detection frame of a camera is generated. At step 620, the data relating to the observed position and the data relating to the pictorial representation is processed, and at step 625, an enhanced pictorial representation, based on the actual positions of the suction ring and the eye, is created.

At step 630, whether to include a graphic relating to ophthalmic surgery is determined. If a graphic relating to ophthalmic surgery is not to be included, then at 650, the enhanced pictorial representation created at step 625 is transmitted for presentation without including a graphic. If a graphic relating to ophthalmic surgery is to be included, then at 655, the pictorial representation created at 625 is transmitted for presentation including a graphic. A graphic for cutting a flap may be used in instances where the surgical procedure requires access to a large area of the cornea. A graphic for making an incision may be used in instances where the surgical procedure requires access to interior structures of the eye, such as the cornea.

As described above in FIGS. 4 and 5, the graphic may also include an angle, a thicker or darker border on a particular section of the graphic, or other symbol to indicate that the suction ring is tilted in relation to the x-y plane. This angle, thicker or darker border, of other symbol used to indicate tilt may be generated by evaluation of data relating to the observed position of the suction ring in relation to the x-y plane. The graphic may be configured to indicate tilt either upward or downward in relation to the x-y plane. For example, as shown in FIG. 4A, the graphic may include angle 415 to indicate that the suction ring is tilted in relation to the x-y plane, and as shown in FIG. 4B, a larger angle 415 indicates a greater degree of tilt. Similarly, for example, the graphic shown in FIG. 5A includes a thickened/darkened border in one section 515 to indicate that the suction ring is tilted in relation to the x-y plane, in the direction of section 515. FIG. 5B contains a much thicker/darker border 515 in the same section to indicate a greater degree of tilt in relation to FIG. 5A, and also in the direction of section 515.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for femtosecond laser ophthalmic surgery comprising:
    a suction ring, the suction ring having a bottom surface that contacts an eye, the bottom surface defining a suction ring plane;
    a patient interface coupled to the suction ring;
    a suction cone coupled to the patient interface;
    a measuring device configured to observe an observed position of the suction ring
and generate data relating to the observed position in an x-y plane, the x-y plane being substantially perpendicular to an apex of a cornea of the eye, the measuring device further operable to observe a tilt angle of the suction ring plane with respect to the x-y plane;
    a camera configured to generate data relating to a pictorial representation of the suction ring and the eye within a detection frame of the camera;
    a processor configure to process data relating to the observed position and data relating to the pictorial representation to create an enhanced pictorial representation based on an actual position of the suction ring and the eye;
    a display configured to receive the enhanced pictorial representation when transmitted from the processor and to present the enhanced pictorial representation during femtosecond laser ophthalmic surgery, the enhanced pictorial representation including a graphic line representing an outline for cutting a flap, the graphic line having a thicker portion, a location of the thicker portion indicating a direction of the tilt angle, a thickness of the thicker portion representing a magnitude of the angle, a greater thickness indicating a greater magnitude.

2. The system of claim 1, wherein the suction ring includes markings to aid in detection or observation by the camera.

3. The system of claim 1, wherein the suction ring contacts a suction cone, the suction cone including at least one force transducer operable to observe an observed point of contact and generate data relating to the observed point of contact.

4. The system of claim 1, wherein the measuring device is a cable-connected or wireless device.

5. The system of claim 1, wherein the measuring device comprises a cable-connected gyroscopic sensor, or a wireless gyroscopic sensor and wireless gyroscopic receiver.

6. The system of claim 1, wherein the measuring device comprises an ultrasonic system.

7. The system of claim 1, wherein the camera comprises an eye tracking system, the eye tracking system operable to observe an alignment of the suction ring in an x-y plane by stereoscopic detection.

8. The system of claim 1, wherein the camera comprises an eye tracking system, the eye tracking system operable to observe an alignment of the suction ring in an x-y plane by object recognition.

9. The system of claim 1, wherein the camera comprises an autofocus camera.

10. The system of claim 1, wherein the processor is operable to create and the display is operable to present the enhanced pictorial representation in real time.

11. The system of claim 1, wherein the processor is further operable to create and the display is operable to present the enhanced pictorial representation including a graphic relating to ophthalmic surgery.

12. The system of claim 1, wherein the display comprises a screen, a heads-up display, or a combination thereof.

13. A method for docking a suction ring in femtosecond laser ophthalmic surgery, the method comprising:
    observing, using a measuring device, an observed position of a suction ring in an x-y plane defined with respect to an eye, the x-y plane being substantially perpendicular to an apex of a cornea of the eye, the suction ring having a bottom surface that contacts the eye, the bottom surface defining a suction ring plane;
    observing, using the measuring device, a tilt angle of the suction ring plane with respect to the x-y plane;
    generating data relating to the observed position of the suction ring using the measuring device, the observed position in the x-y plane;
    generating data relating to a pictorial representation of the suction ring and an eye within a detection frame of a camera;
    processing the data relating to the observed position of the suction ring and data relating to the pictorial representation to create an enhanced pictorial representation based on an actual position of the suction ring and the eye; and transmitting the enhanced pictorial representation from the processor to a display that presents the pictorial representation, the enhanced pictorial representation including a graphic line representing an outline for cutting a flap, the graphic line having a thicker portion, a location of the thicker portion indicating a direction of the tilt angle, an indication of the tilt angle, a thickness of the thicker portion representing a magnitude of the tilt angle, a greater thickness indicating a greater magnitude.

14. The method of claim 13, wherein creating and transmitting the enhanced pictorial representation is in real time.

15. The method of claim 13, wherein transmitting the enhanced pictorial representation from the processor to the display includes transmitting the enhanced pictorial representation with a graphic relating to ophthalmic surgery.

\* \* \* \* \*